United States Patent [19]
Fox et al.

[11] Patent Number: 5,820,604
[45] Date of Patent: Oct. 13, 1998

[54] CANNULA CAP INCLUDING YEILDABLE OUTER SEAL AND FLAPPER VALVE

[75] Inventors: Richard Q. Fox; Larry A. Gilstrap, both of Orlando, Fla.

[73] Assignee: Endolap, Inc., Orlando, Fla.

[21] Appl. No.: 661,484

[22] Filed: Jun. 11, 1996

[51] Int. Cl.⁶ ................................................. A61M 25/00
[52] U.S. Cl. ......................... 604/256; 604/167; 604/264; 604/249; 604/246; 604/169; 137/847; 137/849; 251/149.2; 215/DIG. 3; 215/296; 215/316; 215/320
[58] Field of Search ..................... 604/164, 167, 604/256, 905, 264, 249, 245–247, 169, 165; 137/846, 847, 849, 230, 852, 855; 251/149.1, 149.2; 606/108, 185; 215/317, 296, DIG. 3, 316, 320, 355

[56] References Cited

U.S. PATENT DOCUMENTS

| | | | |
|---|---|---|---|
| 3,991,904 | 11/1976 | Davis et al. | 220/334 |
| 5,044,401 | 9/1991 | Giesler et al. | 137/614.03 |
| 5,092,857 | 3/1992 | Fleischhacker | 604/256 |
| 5,104,383 | 4/1992 | Schichman | 604/167 |
| 5,141,498 | 8/1992 | Christian | 604/167 |
| 5,180,373 | 1/1993 | Green et al. | 604/167 |
| 5,226,426 | 7/1993 | Yoon | 128/753 |
| 5,269,763 | 12/1993 | Boehmer et al. | 604/167 |
| 5,273,545 | 12/1993 | Hunt et al. | 604/167 |
| 5,281,197 | 1/1994 | Arias et al. | 604/57 |
| 5,290,245 | 3/1994 | Dennis | 604/167 |
| 5,300,033 | 4/1994 | Miller | 604/167 |
| 5,312,362 | 5/1994 | Pfolsgraf et al. | 604/167 |
| 5,330,437 | 7/1994 | Durman | 604/167 |
| 5,342,315 | 8/1994 | Rowe et al. | 604/167 |
| 5,364,372 | 11/1994 | Danks et al. | 604/264 |
| 5,380,288 | 1/1995 | Hart et al. | 604/167 |
| 5,385,553 | 1/1995 | Hart et al. | 604/167 |
| 5,385,560 | 1/1995 | Wulf | 604/264 |
| 5,391,153 | 2/1995 | Haber et al. | 604/167 |
| 5,407,433 | 4/1995 | Loomas | 604/167 |
| 5,409,463 | 4/1995 | Thomas et al. | 604/167 |
| 5,411,483 | 5/1995 | Loomas et al. | 604/167 |
| 5,437,646 | 8/1995 | Hunt et al. | 604/167 |
| 5,443,452 | 8/1995 | Hart et al. | 604/167 |
| 5,514,098 | 5/1996 | Pfaslgraf et al. | 604/167 |
| 5,545,150 | 8/1996 | Danks et al. | 604/256 |
| 5,613,663 | 3/1997 | Schmidt et al. | 251/149.2 |
| 5,628,732 | 5/1997 | Antoon, Jr. et al. | 604/167 |
| 5,693,031 | 12/1997 | Ryan et al. | 604/167 |

*Primary Examiner*—Corrine M. McDermott
*Assistant Examiner*—Cris L. Rodriguez
*Attorney, Agent, or Firm*—Allen, Dyer, Doppelt, Milbrath & Gilchrist, P.A.

[57] ABSTRACT

A cannula cap embodiment includes a monolithic elastomeric cap body having a sidewall portion for engaging a proximal end of a cannula, and an end portion connected to the cylindrical sidewall portion. The cannula cap also includes a monolithic flapper valve positioned within an interior of the cap body. The monolithic flapper valve includes a flapper portion, a ringed-shaped flapper mounting portion connected to adjacent interior portions of the cap body, and an integrally formed hinge portion connecting the flapper mounting portion to the flapper portion for permitting the flapper portion to move to an open position when an instrument is positioned within the instrument receiving passageway, and for biasing the flapper portion toward a closed position when an instrument is removed from the instrument receiving passageway. An instrument seal portion of the end portion of the cap body includes a reduced thickness wall portion adjacent an outer opening and extending in a plane transverse to the instrument receiving passageway, and an outwardly extending pleat surrounding the reduced thickness wall portion. The end portion of the cap body also includes a generally planar outer annular portion surrounding the pleat generally aligned with an imaginary plane defined by the reduced thickness wall portion.

37 Claims, 3 Drawing Sheets

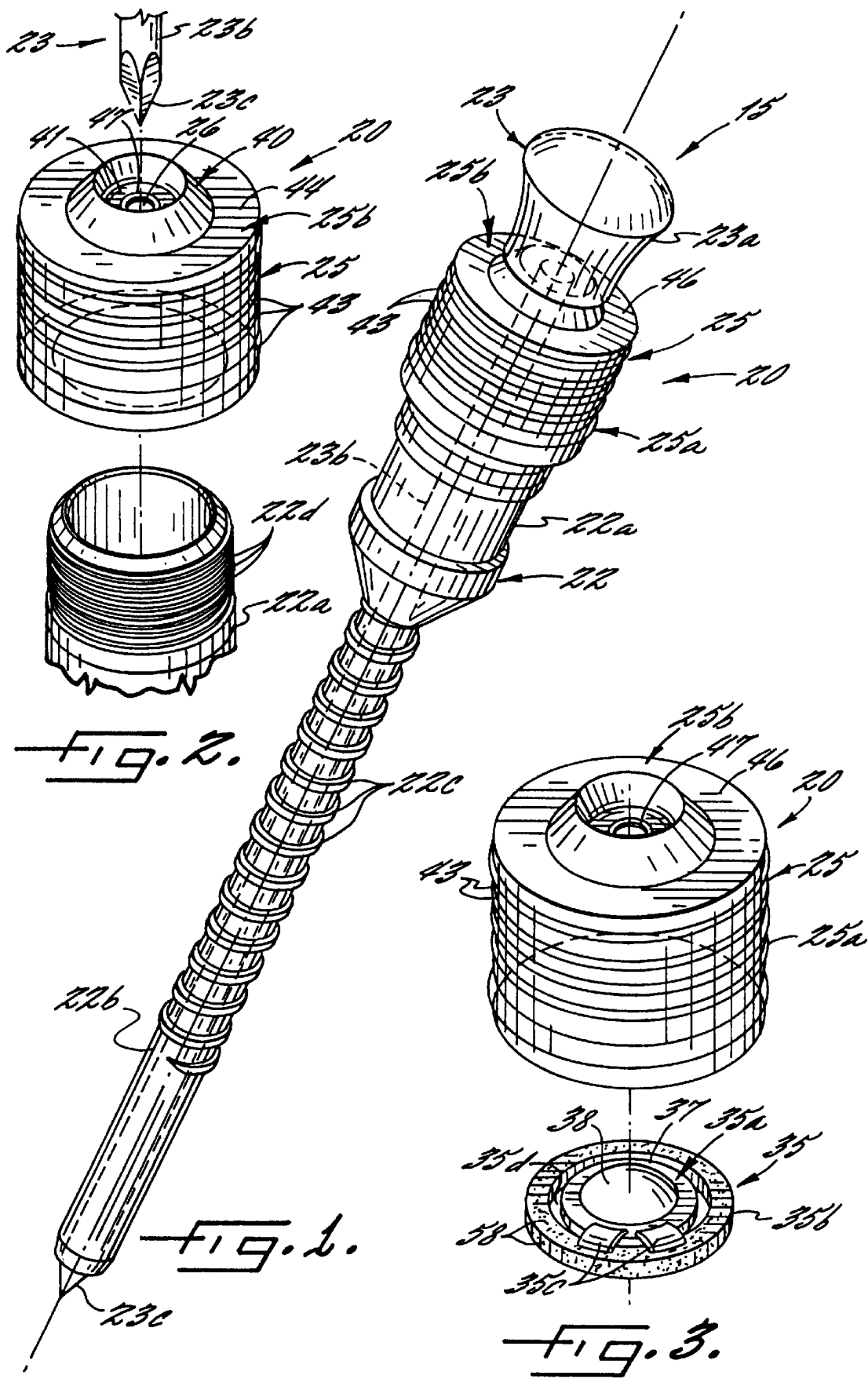

CANNULA CAP INCLUDING YEILDABLE OUTER SEAL AND FLAPPER VALVE

FIELD OF THE INVENTION

The present invention relates to the field of medical devices and, more particularly, to a cannula cap for a cannula.

BACKGROUND OF THE INVENTION

A cannula or trocar tube is typically used in laparoscopic surgery to be inserted into and line an opening made in the body. In other words, a cannula provides a portal into a region within the body, such as the abdominal region, for example. A surgical trocar is a sharp pointed instrument typically initially inserted into a cannula with its pointed tip extending outwardly from a distal end of the cannula. The sharp tip facilitates penetration of the tissue of the body and positioning of the distal end of the cannula into the desired portion of the body. The trocar may be removed and a surgical instrument or endoscope may be inserted into and manipulated while extending through the cannula.

To increase visibility and instrument access within the body, a pressurized gas is typically introduced into the body to define a surgical cavity into which one or more cannulas may extend. Accordingly, the cannula typically requires a seal against a loss of pressurized gas both when no instrument is positioned within the cannula, and also when an instrument is positioned in the cannula. In addition, it may also be desirable to ensure a good gas seal with a shaft of the instrument even as the instrument is manipulated longitudinally into or out of the cannula, or as the instrument is moved in a lateral or side-to-side motion.

One conventional approach to sealing an instrument passageway through a cannula when no instrument is present provides a flapper valve within the upper end or cap of the cannula. For example, U.S. Pat. No. 5,104,383 to Shichman discloses a flapper valve with a raised center portion for effecting sealing with a valve seat defined by a valve mounting portion, and with the flapper being pivotally mounted to the surrounding mounting portion by a pivot pin. Along these lines, U.S. Pat. No. 5,290,245 to Dennis discloses a flapper valve including a domed valve plug, a bias spring for biasing the flapper to the closed position, and a hinge pin for pivotally connecting the flapper to an adjacent mounting portion.

U.S. Pat. No. 5,364,372 to Danks et al. discloses a flat flapper valve connected via a pivot pin and including a bias spring and associated lever arm. U.S. Pat. No. 5,411,483 to Loomas et al. also discloses a spring-loaded flapper valve having a flat flap portion. U.S. Pat. No. 5,385,553 to Hart et al. and U.S. Pat. No. 5,385,560 to Wulf also disclose conventional flat flapper valves oriented at an inclined angle and pivotally connected to the surrounding cap structure. Unfortunately, conventional flapper valves as have been used to seal a cannula require several individual parts which are typically independently manufactured and which are then assembled, such as by precise alignment and insertion of the relatively small hinge pin through the flapper and mounting openings to form the flapper valve.

Relating to the instrument entrance seal of a cannula, elastomeric materials have been used in a cannula cap to permit an instrument to pass through a suitable opening in the elastomeric material and while forming a seal with the instrument. For example, U.S. Pat. No. 5,330,437 to Durman discloses an elastomeric self-sealing valve having an undersized outer opening. U.S. Pat. No. 5,380,288 to Hart et al. discloses an outer seal that permits movement while an inner seal is more rigid to effect complete sealing.

U.S. Pat. No. 5,411,483 to Loomas et al., discussed briefly above, discloses various seal embodiments including an annular corrugated portion or bellows for facilitating lateral movement of an instrument at the outer seal of a cannula cap. Unfortunately, the cannula cap and bellows disclosed in the Loomas et al. patent, for example, includes a multiplicity of individual component parts requiring assembly. In particular, the seal disclosed in the Loomas et al. patent is mounted to a ring, in turn, which is captured for lateral movement by a pair of opposing walls.

In addition to mechanical and assembly complexity of many conventional cannula caps, the manufacturing costs for such caps can be relatively high. Accordingly, the relatively expensive cannula caps are desirably sterilized to permit multiple uses. However, in view of small pockets and other areas within the caps, sterilization of complicated components may also be relatively difficult.

SUMMARY OF THE INVENTION

In view of the foregoing background, it is therefore an object of the present invention to provide a cannula cap having a reliable and effective valve for sealing the instrument receiving passageway of the cannula cap and cannula when no instrument is present, and wherein the valve is readily manufactured and assembled with any other components of the cannula cap.

It is another object of the invention to provide a cannula cap having an outer instrument seal that provides effective sealing for different sized instruments, and which permits side-to-side movement of the instrument within the cannula and while maintaining an effective gas seal, and wherein the cannula cap is readily manufactured.

It is yet another object of the present invention to provide a cannula cap which is readily and inexpensively manufactured to permit disposal after one use if desired.

These and other objects, features and advantages according to the present invention are provided by a cannula cap comprising in one embodiment a monolithic elastomeric cap body which, in turn, includes a cylindrical sidewall portion for engaging a proximal end of the cannula, and an end portion connected to the sidewall portion. A monolithic flapper valve is preferably positioned within an interior of the cap body. More particularly, the end portion of the cap body has a bore therethrough defining an instrument receiving passageway. In addition, the monolithic flapper valve preferably includes a flapper portion, a flapper mounting portion having a ring shaped and being connected to adjacent interior portions of the cap body, and an integrally formed hinge portion connecting the flapper mounting portion to the flapper portion.

The hinge portion is for permitting the flapper portion to move to an open position when an instrument is positioned within the instrument receiving passageway. The hinge portion also biases the flapper portion toward a closed position when an instrument is removed from the instrument receiving passageway. In other words, the cannula cap may in one embodiment be formed of two monolithic component parts —a cap body and a flapper valve—to facilitate manufacture, and to be reliable and rugged in use.

The flapper portion of the valve may preferably include a generally planar portion and a dome shaped portion connected thereto, and wherein the dome shaped portion extends into the instrument receiving passageway to seal same when the flapper portion is in the closed position. For consistent repeatable sealing, the hinge portion preferably comprises a pair of spaced apart straps or living hinges extending between the flapper mounting portion and the flapper portion. The straps provide for proper sealing of the flapper valve despite any manufacturing or alignment tolerances, for example.

Another aspect of the invention relates to an instrument seal portion of the end portion of the cap body. The instrument seal portion preferably has an outer opening for receiving the instrument therethrough and forming a gas seal therewith. The instrument seal portion preferably comprises yieldable sealing means for permitting movement of the instrument in one or more of a longitudinal direction into or out of the instrument receiving passageway, and a lateral or transverse direction and while maintaining an effective gas seal with the instrument.

The yieldable sealing means may preferably comprise a reduced thickness wall portion adjacent the outer opening and extending in a plane transverse to the instrument receiving passageway. The yieldable sealing means also preferably includes an outwardly extending pleat surrounding the reduced thickness wall portion. The end portion of the cap body also preferably further comprises a generally planar outer annular portion surrounding the pleat and being generally aligned with an imaginary plane defined by the reduced thickness wall portion. In addition, the reduced thickness wall portion may include a circular reinforcing rib or ridge immediately adjacent the outer opening.

The end portion of the cap body may also comprise a throat portion having a distal end defining a valve seat for the flapper portion of the flapper valve. The end portion of the cap body may also have an annular recess surrounding the throat portion and further defining the valve seat for the flapper portion.

The cap body also preferably has a valve receiving channel extending along an interior portion thereof adjacent an interior corner defined at the junction between the end portion and the cylindrical sidewall portion. Accordingly, the flapper mounting portion is readily positioned and secured within the valve receiving channel to thereby securely position the flapper valve in its proper position within the cap body.

The cap body may further include a first series of transverse ribs on an interior thereof for removably securing the cannula cap to the proximal end of the cannula. Similarly, the cannula cap may also include a second series of transverse ribs on an exterior thereof. In one embodiment, the flapper valve preferably comprises a plastic material that is flexible, but which is still more rigid than the elastomeric material of the cap body. The cap body may preferably be formed of an elastomeric material, such as silicone rubber.

A method aspect of the invention is for making a cannula cap for positioning on a proximal end of a cannula of a type for receiving an instrument therethrough. The method preferably comprises the steps of: forming a monolithic elastomeric cap body comprising a sidewall portion for engaging a proximal end of a cannula and an end portion connected to the sidewall portion, the end portion having a bore therethrough defining an instrument receiving passageway; forming a monolithic flapper valve comprising a flapper portion, a flapper mounting portion and an integrally formed hinge portion connecting the flapper mounting portion to the flapper portion; and securing the flapper mounting portion of the monolithic flapper valve within the monolithic elastomeric cap body. The flapper portion is preferably movable to an open position when an instrument is positioned within the instrument receiving passageway and is biased toward a closed position when an instrument is removed from the instrument receiving passageway.

The step of forming the monolithic cap body preferably comprises the step of molding same from an elastomeric material, such as silicone rubber, for example. The step of forming the flapper valve preferably comprises molding same from a plastic material more rigid than the elastomeric material of the cap body.

BRIEF DESCRIPTION OF THE DRAWINGS

FIG. 1 is a perspective view of a cannula and cannula cap, as well as a trocar inserted into the cannula and cap in accordance with the present invention.

FIG. 2 is an enlarged exploded perspective view of the cannula cap, cannula upper end, and trocar tip in accordance with the present invention.

FIG. 3 is an enlarged exploded perspective view of the cannula cap in accordance with the present invention.

DETAILED DESCRIPTION OF THE PREFERRED EMBODIMENTS

Figure 4:
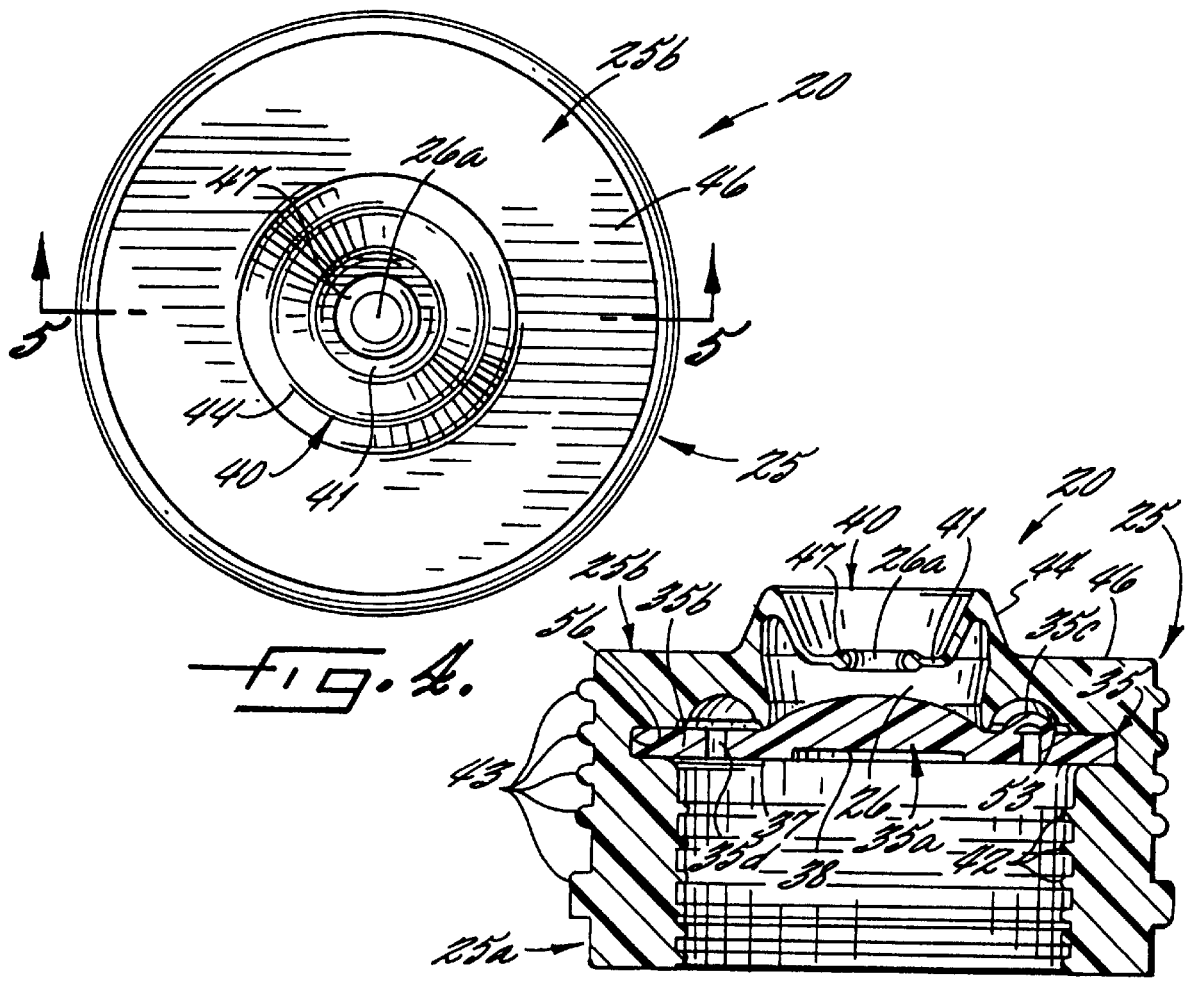
FIG. 4 is a greatly enlarged top plan view of the cannula cap in accordance with the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Referring initially to FIGS. 1–7, the cannula cap 20 in accordance with the invention is first described. FIG. 1 illustrates an instrument assembly 15 including the cannula cap 20 fitted to the upper or proximal end 22a of a cannula 22. The cannula 22 also illustratively includes a reduced diameter tubular portion 22b which, in turn, includes spirally wound ridges 22c thereon, as would be readily understood by those skilled in the art. In addition, the cannula 22 may also include a plurality of transverse circumferentially extending ribs or ridges 22d on the upper end portion 22a to secure the cannula cap 20 to the cannula 22. The cannula 22 may be used for any of a number of minimally invasive surgical techniques, for example, as would be readily understood by those skilled in the art.

A trocar 23 is shown positioned within the cannula 22 and cannula cap 20. The trocar 23 includes an upper handle portion 23a, a shaft portion 23b, and a pointed tip 23c as would also be readily understood by those skilled in the art.

The cannula cap 20 in one preferred embodiment of the invention comprises a monolithic elastomeric cap body 25 which, in turn, includes a sidewall portion 25a for engaging a proximal or adjacent upper end portion 22a of the cannula 22. In other embodiments of the invention, the cap body 25 may comprise more rigid plastic or other materials as will be readily appreciated by those skilled in the art. The cap body 25 also illustratively includes an end portion 25b connected to the cylindrical sidewall portion 25a. More particularly, the end portion 25b of the cap body 25 preferably has a bore 26 therethrough defining an instrument receiving passageway. An instrument tip and shaft, such as the illustrated trocar tip 23c and shaft 23b may be positioned through the bore 26.

The spiked end or tip 23c of the trocar 23 extends outwardly from the end of the cannula 22 when fully inserted as shown in FIG. 1, to thereby facilitate penetration of a portion of the body, such as the abdomen. The trocar 23 may be withdrawn and other instruments inserted through the cannula cap 20 and cannula 22 for various treatment and diagnostic procedures as would be readily understood by those skilled in the art. As used herein the term "instrument" is meant to cover not only hand manipulable endoscopic instruments, but also endoscopes and other medical devices having a shaft portion for extending through the cannula cap 20 and cannula 22.

The cap body 25 may further include a first series of transverse ribs or ridges 42 (FIG. 5) on an interior thereof to facilitate removably securing the cannula cap 20 to the proximal or upper end portion 22a of the cannula 22. In other words, the interior transverse ribs 42 cooperate with the outer ribs 22d on the upper end portion of the cannula to provide a secure fit and seal therewith. In addition, the cannula cap 20 may also include a second series of exterior transverse ridges or ribs 43 on an exterior thereof to facilitate grasping the cannula cap, for example. The exterior ribs 43 may also be useful to permit removably securing a reducer, not shown, to the outside of the cannula cap 20 as shown, for example, in U.S. Pat. No. 5,312,362 to Pfolsgraf et al. The reducer provides a seal with a smaller diameter instrument as would be readily understood by those skilled in the art. The reducer may take the form of an enlarged cannula cap 20, but without the flapper valve 35. Those of skill in the art will also readily appreciate other equivalent projections for removably securing the cannula cap 20 to the cannula 22, and facilitating grasping of the cannula cap 20 or removably securing a reducer to the cap.

A monolithic flapper valve 35 is preferably positioned within an interior of the cap body 25. As will be readily appreciated by those skilled in the art the cannula cap 20 may be formed of two monolithic component parts, namely the cap body 25 and the flapper valve 35, to thereby facilitate manufacturing and to be reliable and rugged in use. The cap body 25 may preferably be formed of an elastomeric material, such as silicone rubber. The flapper valve 35 preferably comprises a plastic material that is flexible yet which is more rigid than the material of the cap body 25.

The monolithic flapper valve 35 illustratively includes a flapper portion 35a, a ring shaped flapper mounting portion 35b being connected to adjacent interior portions of the cap body 25, and an integrally formed hinge portion or pair of hinges 35c connecting the flapper mounting portion to the flapper portion. The hinge portion is preferably formed by the illustrated pair of spaced apart straps or spaghetti hinges 35c extending between the flapper mounting portion 35b and the flapper portion 35a. Those of skill in the art will recognize that a single hinge or multiple hinges are also contemplated by the present invention, although benefits are provided by the illustrated pair of spaced apart hinges 35c.

Figure 5:
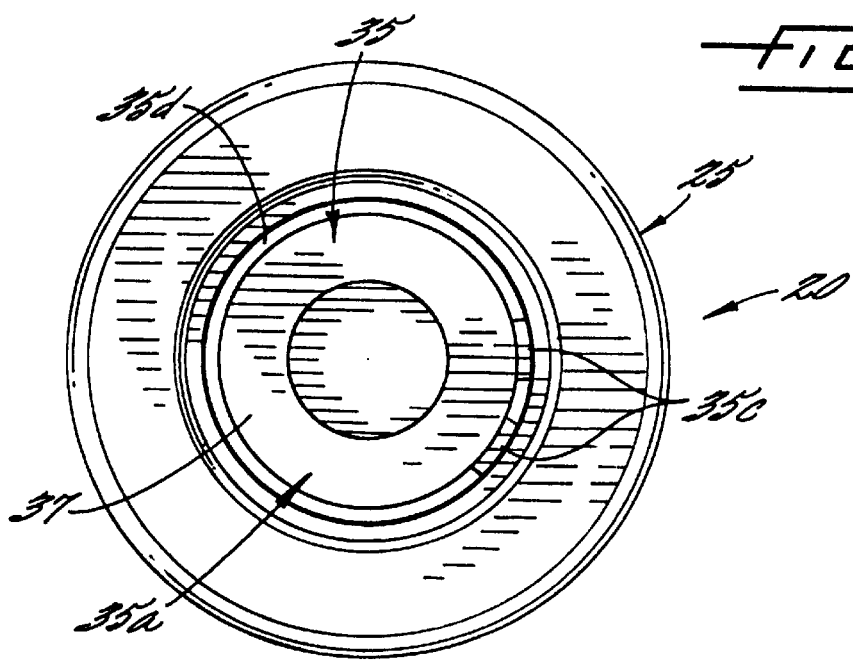
FIG. 5 is a side cross-sectional view taken along lines 5—5 of FIG. 4.
Figure 6:
FIG. 6 is a greatly enlarged bottom plan view of the cannula cap in accordance with the present invention.
Figure 7:
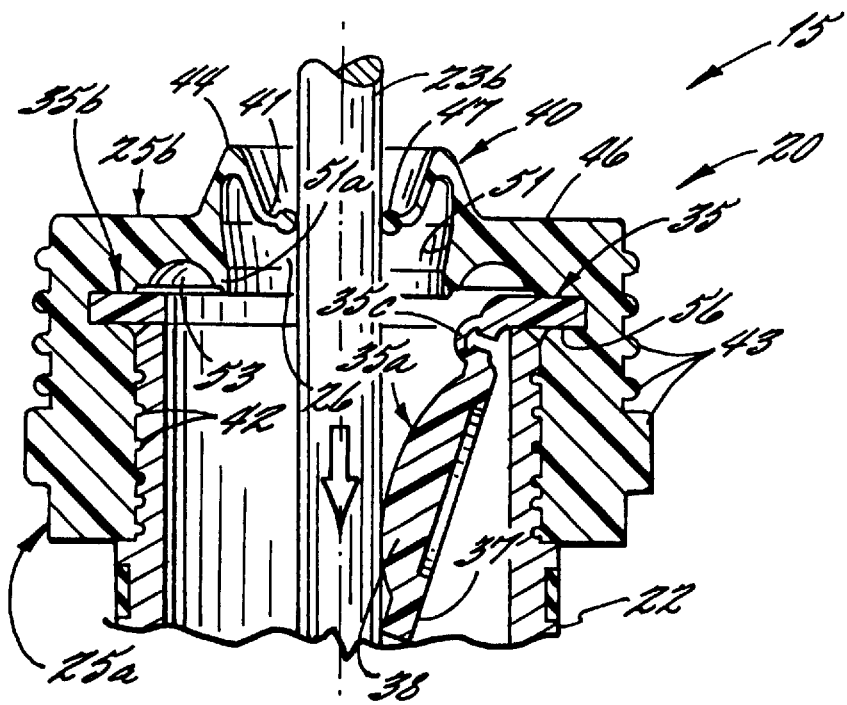
FIG. 7 is a greatly enlarged side cross-sectional view of the cannula cap, cannula, and an instrument shaft being inserted straight into the cap and cannula in accordance with the present invention.

As will be readily appreciated by those skilled in the art, the hinges 35c are for permitting the flapper portion 35a to move or be deflected to an open position when an instrument is positioned within the instrument receiving passageway or bore 26 as shown perhaps best in FIG. 7. The flapper portion 35a of the flapper valve 35 presses lightly against the shaft 23b without adversely restricting or effecting the feel of the shaft when inserted or manipulated within the cannula 22. The hinges 35c also bias the flapper portion 35a toward a closed position when an instrument is removed from the instrument receiving passageway (FIG. 5). As would be readily understood by those skilled in the art, gas back pressure from within the body cavity also serves to fully close the flapper valve 35. A gap 35d is preferably defined between the adjacent edges of the flapper portion 35a and the flapper mounting portion 35b to provide clearance for opening and closing of the flapper portion.

The flapper portion 35a may preferably include a generally planar portion 37 and a dome shaped portion 38 connected thereto. The dome shaped portion 38 may preferably extend into and close off the instrument receiving passageway 26 to seal same when the flapper valve 35 is in the closed position. The combination of the flapper valve 35 and cap body 25 provides for compliance in manufacturing so that the individual components may be made to relatively large tolerances, yet which precisely cooperate together to define the needed gas tight seals once assembled. In other words, the hinges 35c and other components of the flapper valve 35, for example, cooperate with the cap body 25 to allow repeated alignment so that high tolerance valve seating is achieved by low manufacturing tolerance components. The hinges 35c allow the flapper portion 35a to seat itself regardless of any mis-shaping of the dome portion 38, for example.

Figure 8:
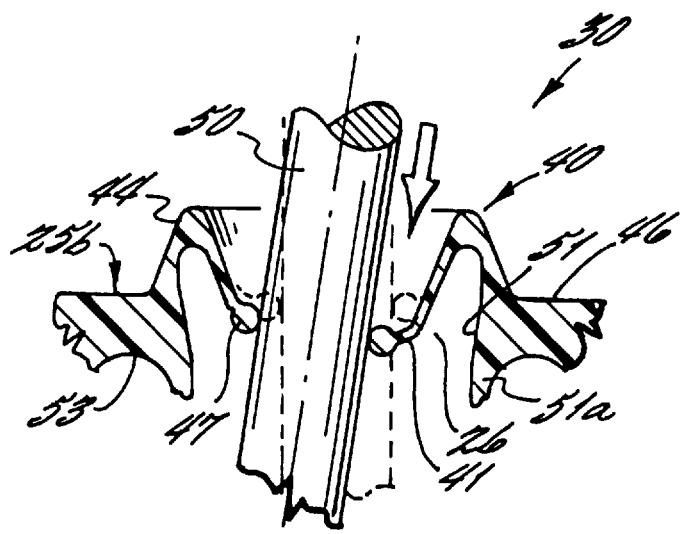
FIG. 8 is a greatly enlarged side cross-sectional view of a portion of the cannula cap and an instrument shaft being manipulated into the cap at an angle in accordance with the present invention.
Figure 9:
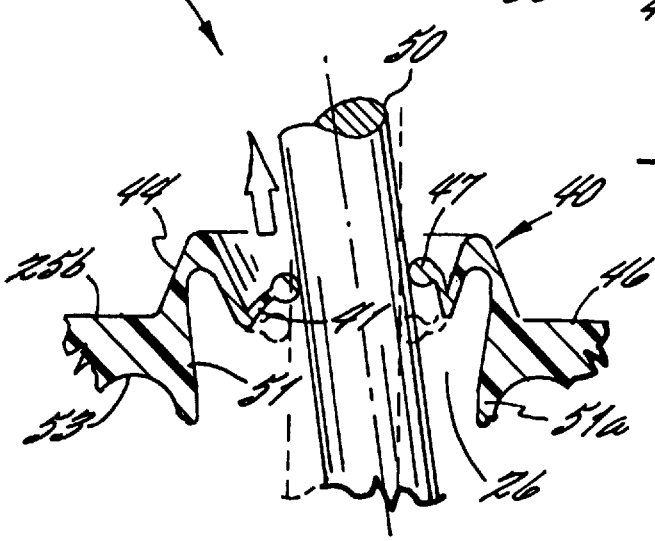
FIG. 9 is a greatly enlarged side cross-sectional view of a portion of the cannula cap and an instrument shaft being manipulated and withdrawn from the cap at an angle in accordance with the present invention.

Turning now additionally to the assembly 30 shown in FIGS. 8 and 9, another aspect of the invention relates to an instrument seal portion 40 of the end portion 25a of the cap body 25. In FIGS. 8 and 9 the angular articulation of the shaft 50 is exaggerated for clarity of explanation as will be readily appreciated by those skilled in the art. The instrument seal portion 40 preferably has an outer opening 26a for receiving the instrument shaft 50 therethrough and forming a gas seal therewith. The instrument shaft 50 may be part of any of a number of medical instruments or devices as would be readily understood by those skilled in the art.

The instrument seal portion 40 preferably comprises yieldable sealing means for permitting movement of the instrument shaft 50 in at least one of a longitudinal direction into or out of the instrument receiving passageway, and transverse thereto, and while maintaining an effective gas seal with the instrument. In other words, the seal portion 40 tracks movement of the instrument without leaking. In addition, the yieldable sealing means permits reduced manufacturing tolerances in making the cap body 25 as it relates, for example, to alignment with respect to the cannula internal bore as will be readily understood by those skilled in the art.

The yieldable sealing means preferably includes the illustrated reduced thickness annular wall portion 41 adjacent the outer opening 26a and extending in a plane transverse to the instrument receiving passageway 26. The reduced thickness is relative to other parts of the end portion 25b and/or to the sidewall portion 25a.

The yieldable sealing means also preferably includes the illustrated outwardly extending pleat 44 surrounding the reduced thickness wall portion 41. The pleat 44 may include the inner and outer wall portions joined at their upper ends as illustrated. Multiple such pleats 44 are also contemplated by the invention as would be readily understood by those skilled in the art. The pleat 44 may also include one or more reinforcing ribs, not shown, extending in a generally radial direction for additional strength.

The end portion 25b of the cap body 25 also preferably further comprises a generally planar outer annular portion 46 surrounding the pleat 44 and being generally aligned with an imaginary plane defined by the reduced thickness wall portion 41. In addition, the reduced thickness wall portion 41 may include a circular reinforcing rib 47 immediately adjacent the outer opening 26a. As would be readily understood by those skilled in the art, the opening 26a is preferably slightly undersized for the instrument shaft 50 to be accommodated. The pleat 44, reduced thickness wall portion 41, the reinforcing rib 47, and throat portion 51 cooperate to permit linear shaft movement into and out of the cannula 22, transverse or lateral movement, and combinations of such movements as illustrated in FIGS. 8 and 9, and while providing a gas tight seal with the instrument shaft 50.

The end portion 25b of the cap body 25 also illustratively includes a throat portion 51 having a distal or lower end 51a defining a valve seat for the flapper portion 35a of the flapper valve 35. The end portion 25b of the cap body 25 also illustratively has an annular recess 53 surrounding the throat portion 51 and further defining the valve seat for the flapper portion 35a of the flapper valve 35. The annular recess 53 also serves to provide clearance for the hinges 35c (FIG. 5).

The cap body 25 may also have a valve receiving channel 56 (FIGS. 5 and 7) extending along an interior portion thereof adjacent a corner defined by the end portion 25b and the cylindrical sidewall portion 25a. Accordingly, the flapper mounting portion 35b is readily positioned and secured within the valve receiving channel 56 to thereby securely position the flapper valve in its proper position within the cap body. An adhesive 58, illustrated schematically by the stippling in FIG. 3, may used to adhesively secure the flapper valve 35 in position within the cap body 25 as would be readily appreciated by those skilled in the art.

A method aspect of the invention is for making a cannula cap 20 for positioning on a proximal end of a cannula 22 of a type for receiving an instrument therethrough. The method preferably comprises the steps of: forming a monolithic elastomeric cap body 25 comprising a sidewall portion 25a for engaging a proximal end of a cannula 22, and an end portion 25b connected to the sidewall portion, the end portion having a bore 26 therethrough defining an instrument receiving passageway. The method preferably further comprises forming a monolithic flapper valve 35, which in turn, includes a flapper portion 35a, a flapper mounting portion 35b and an integrally formed hinge portion 35c connecting the flapper mounting portion to the flapper portion. The method also preferably includes the step of mounting the flapper mounting portion 35b within the monolithic elastomeric cap body 25. The flapper portion 35a is preferably movable to an open position (FIG. 7) when an instrument shaft is positioned within the instrument receiving passageway 26 and is biased to a closed position (FIG. 5) when an instrument is removed from the instrument receiving passageway.

The step of forming the monolithic cap body 25 preferably comprises the step of molding same from silicone rubber. The step of forming the flapper valve 35 preferably comprises molding same from a plastic material that is flexible to define a workable hinge portion 35C, yet which is more rigid than the elastomeric material of the cap body 25.

Another method aspect of the present invention is for making a medical device. The method includes the steps of: providing a cannula 22 comprising a tube having a distal end and a proximal end; providing a cap body 25 comprising an end portion 25b having a bore therethrough defining an instrument receiving passageway; and forming a monolithic flapper valve 35 comprising a flapper portion 35a, a flapper mounting portion 35b, and an integrally formed hinge portion 35c. The method further preferably comprises the step of securing the monolithic flapper valve 35 and cap body 25 to the proximal end of the cannula 22 so that the flapper portion 35a is moved to an open position when an instrument is positioned within the instrument receiving passageway and so that the flapper portion is biased toward a closed position when an instrument is removed from the instrument receiving passageway.

The cannula cap 20 according to the invention provides a flapper valve 35 for reliably and effectively sealing the instrument receiving passageway of the cannula cap and cannula when no instrument is positioned within the cannula. In addition, the yieldable sealing means, provided in part by the reduced thickness wall portion 41 and the pleat 44 of the cap body 25, provides effective sealing for an instrument that is positioned within the instrument receiving passageway 26, even when the instrument is moved longitudinally and/or laterally. Moreover, the operator's "feel" in manipulating the instrument is not adversely affected by the yieldable sealing means or the flapper valve 35. The yieldable sealing means can also readily accommodate different sized instruments. The cap body 25 is also readily manufactured and assembled with the flapper valve 35 to form the cannula cap 20.

The cap body 25, as well as the flapper valve 35 may each be readily made from low cost materials by low cost manufacturing methods as will be readily appreciated by those skilled in the art. In addition, assembly of the completed cannula cap 20 is also straightforward and relatively inexpensive. Accordingly, one important feature of the cannula cap 20 of the present invention is that if desired the cap may be used one time and disposed of, so that no sterilization is needed between uses. The cannula cap 20 also readily mates with the illustrated cannula 22 which, in turn, is relatively simple tubular structure that is easy to sterilize for reuse as would also be readily understood by those skilled in the art.

In other embodiments of the invention, the cannula cap may include an integrally formed or monolithic cap body and flapper valve as would be readily understood by those skilled in the art. In slightly different terms, the cannula cap may include the outer seal portion and while the flapper portion may be integrally molded with the cap body. Many other modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

It is claimed:

1. A cannula cap for positioning on a proximal end of a cannula of a type for receiving an instrument therethrough, said cannula cap comprising:

a monolithic elastomeric cap body comprising a cylindrical sidewall portion for engaging a proximal end of a cannula, an interior portion for receiving a valve, and an end portion connected to said sidewall portion, said end portion having a bore therethrough defining an instrument receiving passageway, said cap body further including a series of transverse ribs on an exterior thereof; and a monolithic flapper valve positioned within the interior portion of said cap body and comprising a flapper portion, a flapper mounting portion having a ring shaped and being connected to the interior portion of said cap body, and an integrally formed hinge portion connecting said flapper mounting portion to said flapper portion for permitting said flapper portion to move to an open position when an instrument is positioned within the instrument receiving passageway and for biasing said flapper portion toward a closed position when an instrument is removed from said instrument receiving passageway, said hinge portion having a plurality of spaced apart straps extending between said flapper mounting portion and said flapper portion.

2. A cannula cap according to claim 1 wherein said end portion further comprises an instrument seal portion having an outer opening for receiving the instrument therethrough and forming a gas seal therewith.

3. A cannula cap according to claim 2 wherein said instrument seal portion comprises yieldable sealing means for permitting movement of the instrument in at least one of a direction of the instrument receiving passageway and transverse thereto and while maintaining the gas seal with the instrument.

4. A cannula cap according to claim 3 wherein said yieldable sealing means comprises a reduced thickness wall portion adjacent the outer opening and extending in a plane transverse to the instrument receiving passageway.

5. A cannula cap according to claim 4 wherein said yieldable sealing means further comprises an outwardly extending generally circular pleat surrounding the reduced thickness wall portion.

6. A cannula cap according to claim 5 wherein said end portion further comprises a generally planar outer annular portion surrounding said pleat and being generally aligned with an imaginary plane defined by said reduced thickness wall portion.

7. A cannula cap according to claim 4 wherein said reduced thickness wall portion further comprises a circular reinforcing rib immediately adjacent the outer opening.

8. A cannula cap according to claim 1 wherein said end portion of said cap body comprises a throat portion having a distal end defining a valve seat for said flapper portion.

9. A cannula cap according to claim 8 wherein said end portion of said cap body further has an annular recess surrounding said throat portion and further defining the valve seat for the flapper portion.

10. A cannula cap according to claim 1 wherein said flapper portion comprises a generally planar portion and a dome shaped portion connected thereto, and wherein said dome shaped portion extends into the instrument receiving passageway to seal same when said flapper portion is in the closed position.

11. A cannula cap according to claim 1 wherein said cap body has a generally circular valve receiving channel extending along the interior portion thereof; and wherein said flapper mounting portion is positioned within said valve receiving channel.

12. A cannula cap according to claim 1 wherein said cap body further includes a series of transverse ribs on the interior portion thereof for removably securing the cannula cap to the proximal end of the cannula.

13. A cannula according to claim 1 wherein said flapper valve comprises a flexible plastic material more rigid than elastomeric material of said cap body.

14. A cannula cap according to claim 1 wherein said cap body comprises silicone rubber.

15. A cannula cap for positioning on a proximal end of a cannula of a type for receiving an instrument therethrough, said cannula cap comprising:

a monolithic elastomeric cap body comprising a sidewall portion for engaging a proximal end of a cannula, and an end portion connected to said sidewall portion, said end portion having a bore therethrough defining an instrument receiving passageway, said end portion further comprising an instrument seal portion having an outer opening for receiving the instrument therethrough and forming a gas seal therewith, said cap body further including a series of transverse ribs on an exterior thereof, said instrument seal portion comprising a reduced thickness wall portion adjacent the outer opening and extending in a plane transverse to the instrument receiving passageway, an outwardly extending pleat surrounding the reduced thickness wall portion, and a generally planar outer portion surrounding said pleat and being generally aligned with an imaginary plane defined by said reduced thickness wall portion; and a flapper valve positioned within an interior of said cap body and movable between an open position when an instrument is positioned within the instrument receiving passageway and a closed position when an instrument is removed from the instrument receiving passageway, said flapper valve having a hinge portion including a plurality of spaced apart straps.

16. A cannula cap according to claim 15 wherein said reduced thickness wall portion further comprises a reinforcing rib immediately adjacent the outer opening.

17. A cannula cap according to claim 15 wherein said flapper valve is a monolithic flapper valve comprising:

a flapper portion;

a flapper mounting portion being connected to adjacent interior portions of said cap body; and an integrally formed hinge portion connecting said flapper mounting portion to said flapper portion for permitting said flapper portion to move to the open position when an instrument is positioned within the instrument receiving passageway and for biasing said flapper portion toward the closed position when an instrument is removed from said instrument receiving passageway.

18. A cannula cap according to claim 17 wherein said end portion of said cap body comprises a throat portion having a distal end defining a valve seat for said flapper portion.

19. A cannula cap according to claim 18 wherein said end portion of said cap body further has a recess surrounding said throat portion and further defining the valve seat for the flapper portion.

20. A cannula cap according to claim 17 wherein said flapper portion comprises a generally planar portion and a dome shaped portion connected thereto, and wherein said dome shaped portion extends into the instrument receiving passageway to seal same when said flapper portion is in the closed position.

21. A cannula cap according to claim 17 wherein said cap body has a valve receiving channel extending along an interior portion thereof adjacent a corner defined between said end portion and said cylindrical sidewall portion; and wherein said flapper mounting portion is positioned within said valve receiving channel.

22. A cannula cap according to claim 15 wherein said cap body further includes a series of transverse ribs on an interior thereof for removably securing the cannula cap to the proximal end of the cannula.

23. A cannula according to claim 15 wherein said flapper valve comprises a flexible plastic material more rigid than said cap body.

24. A cannula cap for positioning on a proximal end of a cannula of a type for receiving an instrument therethrough, said cannula cap comprising:
   a cap body for engaging a proximal end of a cannula, said cap body comprising an end portion having a bore therethrough defining an instrument receiving passageway, said cap body further including a series of transverse ribs on an exterior thereof; and
   a monolithic flapper valve positioned adjacent said cap body and comprising
      a flapper portion,
      a flapper mounting portion positioned adjacent said cap body, and
      an integrally formed hinge portion connecting said flapper mounting portion to said flapper portion for permitting said flapper portion to move to an open position when an instrument is positioned within the instrument receiving passageway and for biasing said flapper portion toward a closed position when an instrument is removed from said instrument receiving passageway, said hinge portion having a plurality of spaced apart straps extending between said flapper mounting portion and said flapper portion.

25. A cannula cap according to claim 24 wherein said cap body is a monolithic body comprising an elastomeric material.

26. A cannula cap according to claim 24 wherein said end portion further comprises an instrument seal portion having an outer opening therethrough in fluid communication with the instrument receiving passageway, and wherein said instrument seal portion comprises:
   a reduced thickness wall portion adjacent the outer opening and extending in a plane transverse to the instrument receiving passageway;
   an outwardly extending pleat surrounding the reduced thickness wall portion; and
   a generally planar outer portion surrounding said pleat and being generally aligned with an imaginary plane defined by said reduced thickness wall portion.

27. A cannula cap according to claim 24 wherein said end portion includes a throat portion having a distal end defining a valve seat for said flapper portion; and wherein said end portion further has a recess surrounding said throat portion and further defining the valve seat for the flapper portion.

28. A cannula cap according to claim 24 wherein said cap body comprises a sidewall portion connected to said end portion; wherein said cap body has a valve receiving channel extending along an interior portion thereof adjacent a corner defined between said end portion and said sidewall portion; and wherein said flapper mounting portion is positioned within said valve receiving channel.

29. A cannula according to claim 24 wherein said flapper valve comprises a plastic material more rigid that said cap body.

30. A cannula cap according to claim 24 wherein said cap body comprises a sidewall portion connected to said end portion; wherein said sidewall portion of said cap body has a generally cylindrical shape; and wherein said flapper mounting portion has a ring shape.

31. A medical device for insertion into a body and comprising:
   a cannula comprising a tube having a distal end and a proximal end; and
   a cannula cap connected to the proximal end of said cannula, said cannula cap comprising
      a cap body comprising an end portion having a bore therethrough defining an instrument receiving passageway, said cap body having a series of transverse ribs on an exterior thereof; and
      a monolithic flapper valve positioned adjacent said cap body and comprising a flapper portion, a flapper mounting portion positioned adjacent said cap body, and an integrally formed hinge portion connecting said flapper mounting portion to said flapper portion for permitting said flapper portion to move to an open position when an instrument is positioned within the instrument receiving passageway and for biasing said flapper portion toward a closed position when an instrument is removed from said instrument receiving passageway, said hinge having a plurality of spaced apart straps extending between said flapper mounting portion and said flapper portion.

32. A medical device according to claim 31 wherein said cap body is a monolithic body comprising an elastomeric material.

33. A medical device according to claim 31 wherein said end portion further comprises an instrument seal portion having an outer opening therethrough in fluid communication with the instrument receiving passageway, and wherein said instrument seal portion comprises:
   a reduced thickness wall portion adjacent the outer opening and extending in a plane transverse to the instrument receiving passageway;
   an outwardly extending pleat surrounding the reduced thickness wall portion; and
   a generally planar outer portion surrounding said pleat and being generally aligned with an imaginary plane defined by said reduced thickness wall portion.

34. A medical device according to claim 31 wherein said end portion includes a throat portion having a distal end defining a valve seat for said flapper portion; and wherein said end portion of said cap body further has a recess surrounding said throat portion and further defining the valve seat for the flapper portion.

35. A medical device according to claim 31 wherein said cap body comprises a sidewall portion connected to said end portion; wherein said cap body has a valve receiving channel extending along an interior portion between said end portion and said sidewall portion; and wherein said flapper mounting portion is positioned within said valve receiving channel.

36. A medical device according to claim 31 wherein said cap body comprises an elastomeric material, and said flapper valve comprises a flexible plastic material more rigid than the elastomeric material of said cap body.

37. A medical device according to claim 31 wherein said cap body comprises a sidewall portion extending from said end portion; wherein said sidewall portion of said cap body has a generally cylindrical shape; and wherein said flapper mounting portion has a ring shape.

* * * * *